US00PP30168P2

(12) United States Plant Patent
Probst

(10) Patent No.: US PP30,168 P2
(45) Date of Patent: Jan. 29, 2019

(54) ***COREOPSIS* PLANT NAMED 'ENCHANTED RED'**

(50) Latin Name: ***Coreopsis* hybrid**
Varietal Denomination: Enchanted Red

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/732,631

(22) Filed: Dec. 6, 2017

(51) Int. Cl.
*A01H 5/02* (2018.01)

(52) U.S. Cl.
USPC ..... Plt./417

(58) Field of Classification Search
USPC ..... Plt./417
See application file for complete search history.

*Primary Examiner* — Annette H Para
(74) *Attorney, Agent, or Firm* — Penny J. Aguirre

(57) ABSTRACT

A new cultivar of hybrid *Coreopsis* named 'Enchanted Red' that is characterized by its compact and densely plant habit reaching an average of 23 cm in height and 50 cm in width, its floriferous and long bloom season; bloom commences in late June and continues until frost in Kensington, Conn., its relative sterility under normal garden conditions without the need for deadheading to keep flowering, and its large solid red flowers in warm and cooler temperatures (for the majority of the growing season in New Braintree, Mass.) with new flowers produced during the heat of summer paler red in color.

2 Drawing Sheets

Botanical classification: *Coreopsis* hybrid.
Variety denomination: 'Enchanted Red'.

BACKGROUND OF THE INVENTION

The present invention relates to a new and distinct cultivar of *Coreopsis* plant, botanically of hybrid origin and known as *Coreopsis* 'Enchanted Red' and will be referred to hereinafter by its cultivar name, 'Enchanted Red'. The new cultivar of *Coreopsis* is an herbaceous perennial grown for landscape and container use.

The new cultivar was discovered by the Inventor in July of 2015 as a naturally occurring branch mutation of *Coreopsis* 'Enchanted Eve' (U.S. Plant Pat. No. 27,857) in a container in Kensington, Conn.

Asexual propagation of the new cultivar was first accomplished by stem cuttings under the direction of the Inventor in New Braintree, Mass. in July of 2015. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Enchanted Red' as a new and distinct cultivar of *Coreopsis*.

1. 'Enchanted Red' exhibits a compact and densely branched plant habit reaching an average of 23 cm in height and 50 cm in width.
2. 'Enchanted Red' exhibits a floriferous and long bloom season; blooming commences in late June and continues until frost in Kensington, Conn.
3. 'Enchanted Red' is relatively sterile under normal garden conditions and does not require deadheading to keep flowering.

4. 'Enchanted Red' exhibits large inflorescences with ray florets that are solid red in color in warm and cooler temperatures (for the majority of the growing season in New Braintree, Mass.) with new flowers produced during the heat of summer paler red in color.

The parent plant of 'Enchanted Red', 'Enchanted Eve', differs from 'Enchanted Red' in having inflorescences with ray florets that are light yellow in color and suffused with red a red eye that expands into the ray floret surface in cooler temperatures. 'Enchanted Red' can also be most compared to the *Coreopsis* cultivars 'Red Elf' (U.S. Plant Pat. No. 27,918) and 'Mercury Rising' (U.S. Plant Pat. No. 24,689). 'Red Elf' is similar to 'Enchanted Red' in having a compact plant habit, large red flowers, and a long bloom season without requiring deadheading. 'Red Elf' differs from 'Enchanted Red' in having inflorescences with ray florets that are deeper red in color that is retained the entire season and in having a narrower and more upright plant habit. 'Mercury Rising' is similar to 'Enchanted Red' in having red ray florets. 'Mercury Rising' differs from 'Enchanted Red' in having a larger, more openly branched plant habit.

BRIEF DESCRIPTION OF THE DRAWINGS

The accompanying colored photographs illustrate the overall appearance and distinct characteristics of the new *Coreopsis*. The plants in the photographs are three months in age (from a 32-cell plug) as grown outdoors in a one-gallon container in New Braintree, Mass.

The photograph in FIG. 1 provides a top view of 'Enchanted Red' in bloom.

Figure 1:
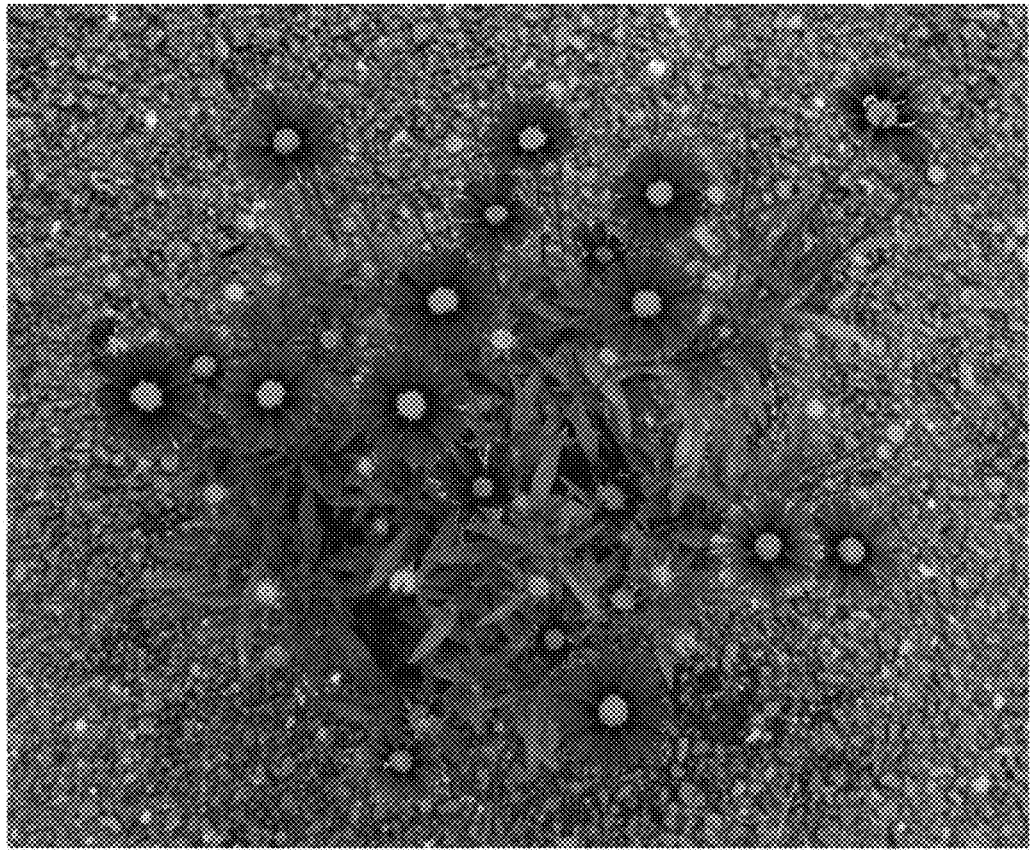
Figure 2:
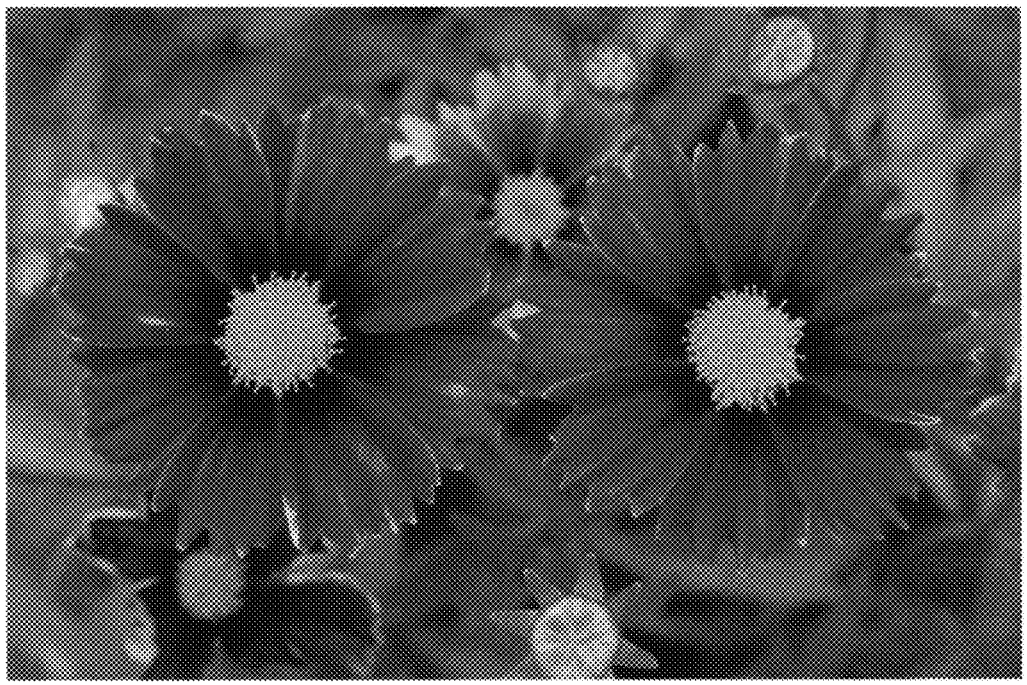

The photograph in FIG. 2 provides a close up view of the inflorescences of 'Enchanted Red'.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of plants of the new cultivar that are three months in age (from a 32-cell plug) as grown outdoors in one-gallon containers in New Braintree, Mass. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms from mid June until frost in Kensington, Conn.

*Plant type*.—Herbaceous perennial.

*Plant habit*.—Compact, clump-forming, and densely branched.

*Height and spread*.—An average of 23 cm in height and 50 cm in width.

*Cold hardiness*.—At least in U.S.D.A Zone 5a.

*Diseases resistance*.—Has been observed to be highly resistant to powdery mildew caused by *Podosphaera macularis*.

*Root description*.—Fibrous when young, becoming more fleshy with age.

*Propagation*.—Stem cuttings.

*Time required for root initiation*.—An average of 10 days for root initiation.

*Growth rate*.—Vigorous, but stays compact.

Stem description:

*Shape*.—Oval, ridged.

*Stem color*.—Young stems; 146C, mature stems; 146C with marking of 187A near the nodes, oldest part of the stem is bark-like and a blend of N199B and 199A.

*Stem size*.—Main stems; an average of 5 cm in length (excluding terminal peduncle) and 2 mm in width, secondary; average of 4 cm in length and 2 mm in width (excluding peduncles).

*Stem surface*.—Young stems; glabrous, mature stems; ridged and bark like.

*Stem aspect*.—Nearly vertical.

*Branching habit*.—An average of 8 main branches, up to 4 secondary branches per main stem.

*Internode length*.—An average of 2 cm.

Foliage description:

*Leaf division*.—Simple.

*Leaf margins*.—Entire to deeply tri-fid (almost leaflet-like).

*Leaf size*.—Variable, up to 4 cm in length and 2 cm in width when tri-fid, up to 4 cm in length and 6 mm in width when entire.

*Leaf shape*.—Lanceolate when entire, lanceolate lobes when tri-fid.

*Leaf base*.—Truncate to stem.

*Leaf apex*.—Acute.

*Leaf venation*.—Pinnate, not prominent, matches leaf color on upper and lower surface.

*Leaf attachment*.—Sessile.

*Leaf arrangement*.—Opposite.

*Leaf surface*.—Glabrous on upper and lower surface.

*Leaf color*.—Young and mature upper surface; 146A, young and mature lower surface; 146B.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray florets, longer in cool temperatures, bracts and disk florets are persistent.

*Fragrance*.—Pleasant fragrance.

*Quantity of inflorescences*.—An average of 10 composite inflorescences per corymb and one corymb per main branch.

*Inflorescence size*.—Corymbs; an average of 8 cm in width and 11 cm in height, composite; an average of 1 cm in depth and up to 4 cm in diameter with disk portion an average of 1 cm in diameter.

*Inflorescence buds*.—An average of 6 mm in depth and in diameter, spherical in shape, color; top 151A blend with 7A in mid-section, base 144A.

*Peduncle*.—An average of 9 cm in length and 1 mm in width, glabrous surface, 144A in color.

Involucral bracts:

*Bract number*.—Two rows of 8.

*Bract arrangement*.—Outer bracts are un-fused and reflexed when flower is fully open and becoming horizontal after ray florets drop, inner bracts are 50% fused and surround receptacle with a campanulate form with apical portion un-fused, spreading, and held close to lower surface of ray florets, 50% is fused at base, free portion is spreading outward and reflexed when flower is fully open, held horizontal after florets have dropped.

*Bract size*.—Outer bracts; an average of 8 mm in length and 3 mm in width, inner bracts 5 mm in length and 4 mm in width.

*Bract color*.—Outer bracts; translucent margins, 144A, inner bracts; base 144A, mid-section to tip 11A and translucent margins.

*Bract texture*.—Glabrous on both surfaces.

*Bract apex*.—Acute.

*Bract base*.—Truncate.

*Bract margins*.—Entire.

*Bract shape*.—Broadly lanceolate.

Ray florets (sterile):

*Number*.—An average of 8 arranged primarily in one row.

*Shape*.—Ovate.

*Size*.—An average of 2.3 cm in length and 1.5 cm in width.

*Apex*.—4 notched.

*Base*.—Broadly cuneate.

*Margins*.—Entire with apex notched.

*Aspect*.—Held horizontal to slightly downward.

*Texture*.—Glabrous on inner and outer surfaces.

*Color*.—Opening and fully open upper surfaces in warm and cool temperatures; 53A with a slight hints of 13A on the tips and heavily suffused with 187A, in hot summer temperatures 46A, with a slight suffusion of 12A, and 12A at apex, opening and fully open lower surfaces; 11A.

Disk florets (perfect):

*Shape*.—Tubular, corolla is fused, flared at apex.

*Number*.—An average of 100.

*Size*.—About 4.5 mm in length and 1 mm in width.

*Color*.—En masse; 21A, corolla; base of tube is 11B in color, flared portion is 17A and translucent.

*Receptacle*.—About 6 mm in diameter and 3 mm in depth, 145C in color.

Reproductive organs:

*Presence*.—Disk florets are perfect, ray florets are sterile.

*Gynoecium*.—1 Pistil, 4 mm in length, style is very fine and about 13B in color and translucent, bifid pilose stigma is 21A in color with branches about 1 mm in length and recurved, ovary is 3 mm in length, 1 mm in width, inferior, and 5C in color.

*Androecium*.—5 stamens, fused into tube surrounding style, 2 mm in length and 0.5 mm in width, 166A in color, no pollen observed.

*Fruit/seed*.—No fruit or seed development was observed, plants have been observed to be nearly sterile.

It is claimed:

1. A new and distinct cultivar of *Coreopsis* plant named 'Enchanted Red' as herein illustrated and described.

* * * * *